US009709508B2

United States Patent
Shibuta et al.

(10) Patent No.: US 9,709,508 B2
(45) Date of Patent: Jul. 18, 2017

(54) METHOD AND APPARATUS FOR INSPECTING LAMINATED IRON CORE

(71) Applicants: MITSUI HIGH-TEC, INC., Fukuoka (JP); TOYOTA JIDOSHA KABUSHIKI KAISHA, Aichi-ken (JP)

(72) Inventors: Tadashi Shibuta, Fukuoka (JP); Masashi Matsumoto, Aichi-ken (JP); Tatsuhiko Mizutani, Aichi-ken (JP); Yoshitada Yamagishi, Aichi-ken (JP)

(73) Assignees: MITSUI HIGH-TEC, INC., Fukuoka (JP); TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 0 days.

(21) Appl. No.: 15/088,620

(22) Filed: Apr. 1, 2016

(65) Prior Publication Data
US 2016/0299087 A1  Oct. 13, 2016

(30) Foreign Application Priority Data
Apr. 9, 2015  (JP) .................. 2015-079975

(51) Int. Cl.
*G01N 21/94* (2006.01)
*G01N 21/88* (2006.01)
*G01N 21/954* (2006.01)

(52) U.S. Cl.
CPC ......... *G01N 21/94* (2013.01); *G01N 21/8851* (2013.01); *G01N 21/954* (2013.01); *G01N 2201/06146* (2013.01); *G01N 2201/105* (2013.01)

(58) Field of Classification Search
CPC .............. G01N 21/94; G01N 21/8851; G01N 2201/105; G01N 2201/06164; G01C 19/42; H02K 7/20; H02K 29/10
See application file for complete search history.

(56) References Cited

U.S. PATENT DOCUMENTS

| | | | |
|---|---|---|---|
| 4,529,900 A * | 7/1985 | Uzuka | H02K 7/20 310/266 |
| 8,110,959 B2 * | 2/2012 | Hultman | H02K 1/02 310/216.113 |
| 9,041,261 B2 | 5/2015 | Yamamoto et al. | |
| 2002/0129651 A1 * | 9/2002 | Burlingame | G01C 19/42 73/504.11 |

(Continued)

FOREIGN PATENT DOCUMENTS

| | | |
|---|---|---|
| JP | 2013-27100 | 2/2013 |
| JP | 2014-176235 | 9/2014 |

*Primary Examiner* — Sang Nguyen
(74) *Attorney, Agent, or Firm* — Greenblum & Bernstein, P.L.C.

(57) ABSTRACT

There is provided a method for inspecting a laminated iron core structured by laminating a plurality of iron core pieces having a predetermined shape and including therein a cooling flow path allowing refrigerant to flow therethrough, the refrigerant being supplied and discharged through openings formed at different positions. The method includes arranging a light projecting part and a light receiving part of a photosensor in the openings of the cooling flow path, respectively, and detecting light from the light projecting part by the light receiving part to thereby inspect a penetrating state of the cooling flow path.

12 Claims, 4 Drawing Sheets

(56) References Cited

U.S. PATENT DOCUMENTS

| | | | |
|---|---|---|---|
| 2003/0090168 A1* | 5/2003 | Takano | H02K 1/16 310/216.045 |
| 2011/0031851 A1* | 2/2011 | Uryu | H02K 11/024 310/68 B |
| 2012/0279313 A1* | 11/2012 | Diatzikis | G01P 5/02 73/861 |
| 2013/0020889 A1 | 1/2013 | Yamamoto et al. | |
| 2013/0270931 A1* | 10/2013 | Handa | H02K 1/32 310/43 |
| 2016/0036276 A1 | 2/2016 | Yamagishi et al. | |

\* cited by examiner

METHOD AND APPARATUS FOR INSPECTING LAMINATED IRON CORE

CROSS REFERENCE TO RELATED APPLICATION(S)

This application is based upon and claims the benefit of priority of Japanese Patent Application No. 2015-79975 filed on Apr. 9, 2015, the contents of which are incorporated herein by reference in its entirety.

BACKGROUND OF THE INVENTION

1. Field of the Invention

The present invention relates to a method and an apparatus for inspecting a laminated iron core configured by a plurality of laminated iron core pieces having a predetermined shape and including therein a cooling flow path allowing refrigerant to flow therethrough.

2. Description of the Related Art

A rotor of a motor or a generator has a problem that a permanent magnet is demagnetized due to the increased temperature of the rotor during rotation, thereby reducing the motor performance.

To cope with this problem, the rotor is cooled using refrigerant such as cooling oil. In addition to a hole formed to penetrate in the axial direction, a penetration hole extending from a shaft hole in the radial direction is used as a cooling flow path for the refrigerant. Here, the permanent magnet is easy to increase in temperature due to accumulated heat in the longitudinal-direction central area. Thus, by cooling the longitudinal-direction central area of the permanent magnet with a higher priority, the cooling efficiency can be enhanced (see, for example, JP-A-2014-176235 and JP-A-2013-027100 as Patent Documents 1 and 2).

Patent Document 1: JP-A-2014-176235
Patent Document 2: JP-A-2013-027100

SUMMARY OF THE INVENTION

While a rotor is being manufactured, when the cooling flow path is clogged because foreign substances are caught in the penetration hole, the refrigerant cannot be supplied into the rotor sufficiently, thereby failing to provide the desired cooling efficiency. Thus, after manufacture of the rotor, the penetrating state of the cooling flow path must be confirmed to assure the product quality.

However, as described above, when the penetration hole of the cooling flow path is formed to extend in the radial direction from the shaft hole and go toward the longitudinal-direction central area of the permanent magnet, visual confirmation of the penetrating state is difficult. Moreover, when the cooling flow path is curved and is not straight, visual confirmation of the penetrating state is also impossible.

The present invention is made in view of the above circumstances and thus has a non-limited object to provide a method and an apparatus capable of inspecting a laminated iron core efficiently and easily even when the penetrating state of the cooling flow path cannot be confirmed visually.

A first aspect of the present invention provides a method for inspecting a laminated iron core structured by laminating a plurality of iron core pieces having a predetermined shape and including therein a cooling flow path allowing refrigerant to flow therethrough, the refrigerant being supplied and discharged through openings formed at different positions, the method including: arranging a light projecting part and a light receiving part of a photosensor in the openings of the cooling flow path, respectively; and detecting light from the light projecting part by the light receiving part to thereby inspect a penetrating state of the cooling flow path.

The method may be implemented such that the cooling flow path includes a first flow path extending perpendicularly to a laminating direction of the laminated iron core and a second flow path communicating with the first flow path and extending in the laminating direction of the laminated iron core, and the light projecting part is arranged in the opening of the first flow path, and the light receiving part is arranged in the opening of the second flow path.

The method may be implemented such that the laminated iron core includes at least one other cooling flow path to form a plurality of cooling flow paths in a circumferential direction of the laminated iron core, and the laminated iron core and the photosensor are relatively rotated about a shaft center of the laminated iron core and the penetrating states of the plurality of cooling flow paths are sequentially inspected.

The method may be implemented such that each first flow path is branched off to have a plurality of branch paths communicating with the second flow path, and at least a same number of the light projecting parts as a number of the plurality of branch paths included in each first flow path are arranged in the openings of the first flow path formed at different positions in the circumferential direction of the laminated iron core, and projection angles of lights from the light projecting parts are adjusted for each of the branch paths.

The method may be implemented such that each first flow path is branched off to have a plurality of branch paths respectively including the openings of the first flow path, and at least a same number of the light projecting parts as a number of the plurality of branch paths included in each first flow path are arranged in the openings of the different branch paths of the first flow paths formed at different positions in the circumferential direction of the laminated iron core, and projection angles of lights from the light projecting parts are adjusted for each of the branch paths.

The method may be implemented such that determination of the penetrating state of the cooling flow path is made using a quantity of light detected by the light receiving part.

A second aspect of the present invention provides an apparatus for inspecting a laminated iron core structured by laminating a plurality of iron core pieces having a predetermined shape and including therein a cooling flow path allowing refrigerant to flow therethrough, the refrigerant being supplied and discharged through openings formed at different positions, the apparatus including: a photosensor including a light projecting part and a light receiving part arranged in the openings of the cooling flow path, respectively, wherein the apparatus detects light from the light projecting part by the light receiving part to thereby inspect a penetrating state of the cooling flow path.

The apparatus may be configured such that the cooling flow path includes a first flow path extending perpendicularly to a laminating direction of the laminated iron core and a second flow path communicating with the first flow path and extending in the laminating direction of the laminated iron core, and the light projecting part is arranged in the opening of the first flow path, and the light receiving part is arranged in the opening of the second flow path.

The apparatus may be configured such that the first flow path includes a plurality of branch paths, at least a same number of light projecting parts as a number of branch paths are arranged, and projection angles of lights from the light projection parts are adjusted for each of the branch paths.

The apparatus may be configured by further including a turntable which rotates the laminated iron core about a shaft center of the laminated iron core.

The apparatus may be configured such that one or both of the light projecting part and the light receiving part include a position adjusting mechanism.

The apparatus may be configured such that one or both of the light projecting part and the light receiving part include an angle adjusting mechanism.

In the laminated iron core inspecting method and apparatus according to the aspects of the present invention, the light projecting and receiving parts of the photosensor are arranged in the openings of the cooling flow paths formed within the laminated iron core, and lights from the light projecting part are detected by the light receiving part, thereby inspecting the penetrating state of the cooling flow path. Thus, even when the penetrating state of the cooling flow path cannot be confirmed visually, the penetrating state can be checked efficiently and easily.

Also, when rotating the laminated iron core about the shaft center thereof, without preparing the same number of photosensors as the number of the multiple cooling flow paths formed in the circumferential direction of the laminated iron core, the multiple cooling flow paths can be moved sequentially to the arranged position of the photosensor (light projecting part and right receiving part). Therefore, the penetrating states of the cooling flow paths can be checked using a smaller number of photosensors than the cooling flow paths. This can simplify facility structure and can reduce facility cost.

DETAILED DESCRIPTION OF THE EXEMPLARY EMBODIMENTS

Next, referring to the accompanying drawings, description is given of embodiments of the present invention for specific understanding of the present invention.

Figure 1A:
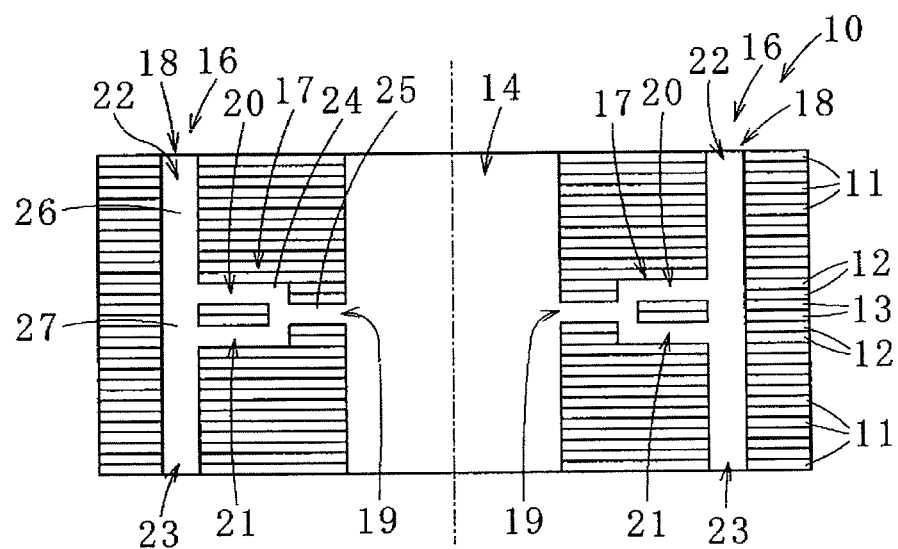
FIGS. 1A, 1B are respectively a side section view and a plan view of a laminated iron core to which a laminated iron core inspecting method according to an embodiment of the present invention is applied.
Figure 1B:
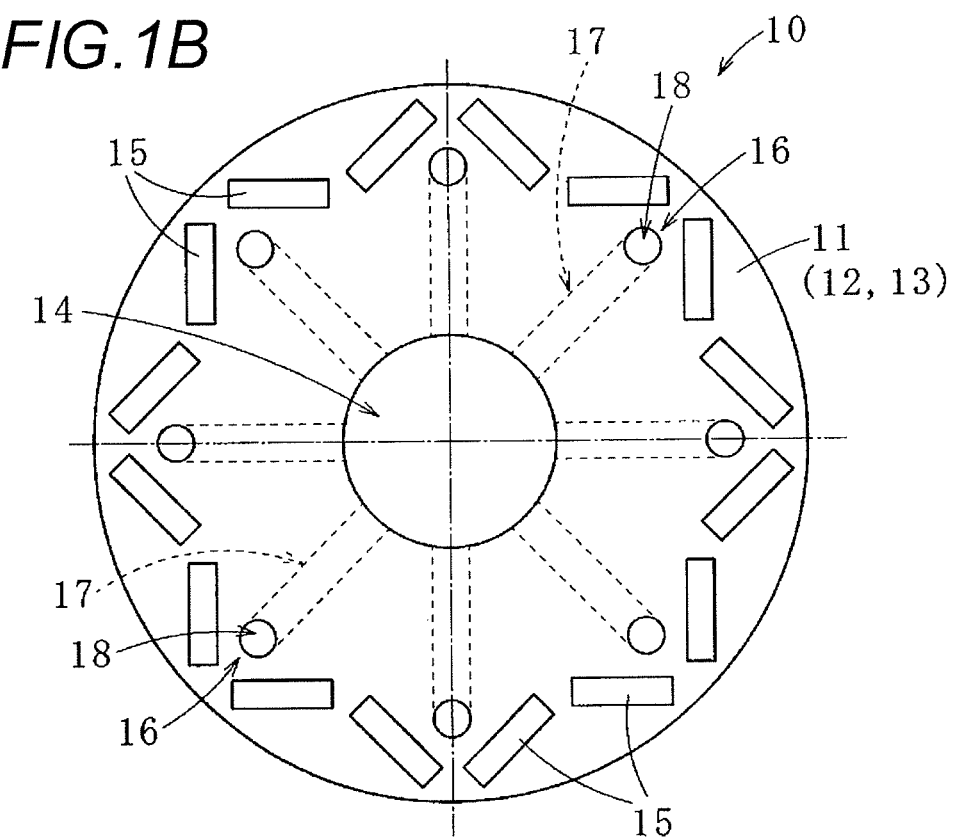
Figure 2:
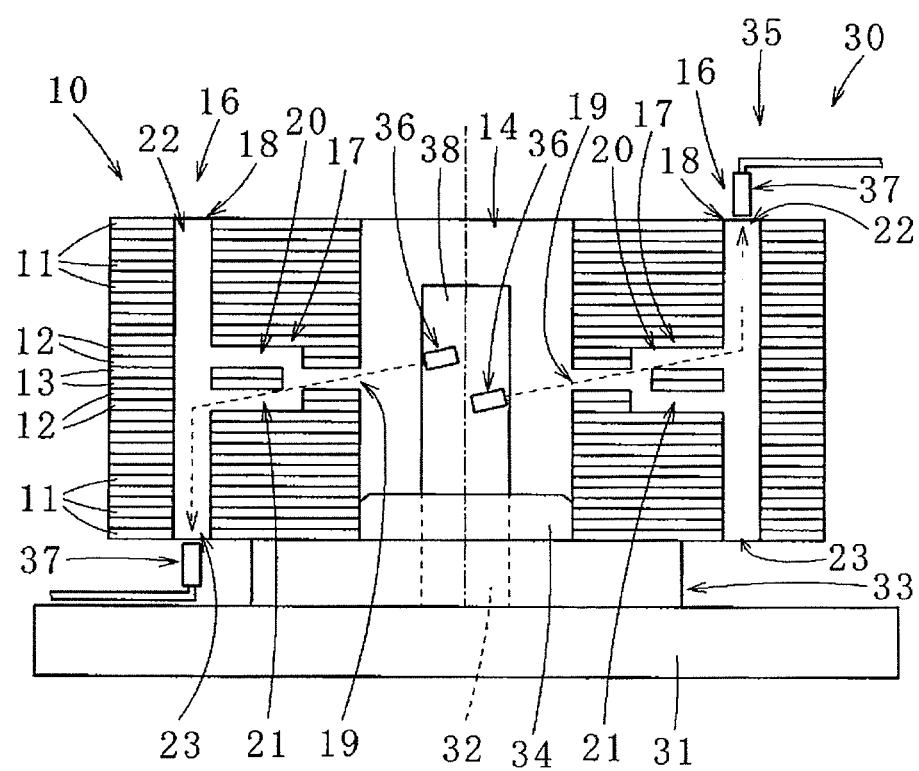
FIG. 2 is an explanatory view of the laminated iron core inspecting method.

Firstly, referring to FIGS. 1A, 1B and 2, description is given of a rotor 10 to which a laminated iron core inspecting method according to an embodiment of the present invention is applied. The rotor 10 is an example of a laminated iron core, and is also called a rotor core.

The rotor 10 is structured by laminating multiple annular-shaped (predetermined shaped) iron core pieces 11 to 13.

Each iron core piece 11 to 13 has an annular integrated structure. Here, the iron core piece may have a split structure capable of connecting multiple arc-shaped iron core piece parts into an annular shape, or a structure capable of connecting the circumferential-direction portions of multiple arc-shaped iron core piece parts in a connecting part and folding the connecting part into an annular shape.

Each of the iron core pieces 11 to 13 is formed by blanking a thin member made of an electromagnetic steel plate or amorphous having a thickness of, for example, about 0.10 to 0.5 mm. Here, the iron core piece may also be formed by blanking a single thin member, or by blanking multiple sheets (for example, two or three or more sheets) of thin members while they are superimposed.

The iron core pieces 11, 11 adjoining each other in the laminating direction (similarly in the other iron core pieces 12, 13) can be connected together using one or two or more methods including caulk, resin (thermosetting resin (for example, epoxy resin) or thermoplastic resin), adhesive, and welding.

In the center of the rotor 10, there is formed a shaft hole 14, and in the periphery of the shaft hole 14 and with the shaft hole 14 as the center, there are formed multiple magnet insertion holes 15 for permanent magnets (not shown) constituted of penetration holes formed in the laminating direction of the rotor 10. Fixation of the permanent magnet into the magnet insertion hole 15 may preferably be carried out using the above resin.

Here, the shaft hole 14 includes a key (a protrusion) (not shown) protruding inward.

Within the rotor 10, multiple identically shaped cooling flow paths 16 for flow of refrigerant (for example, cooling oil) supplied from outside are formed at regular pitches in the circumferential direction of the rotor 10.

Each cooling flow path 16 includes a radial-direction flow path (an example of a first flow path) 17 extending in the radial direction (a direction perpendicular to the laminating direction) of the rotor 10, and a laminating-direction flow path (an example of a second flow path) 18 extending in the laminating direction of the rotor 10.

The radial-direction flow path 17 is formed radially in the laminating-direction central portion of the rotor 10 with the shaft hole 14 as the center thereof. The one end side of the radial-direction flow path 17 is opened toward the shaft hole 14, thereby providing an opening 19 (the refrigerant supply side opening of the cooling flow path 16) communicating with the outside of the rotor 10.

The radial-direction flow path 17 also includes multiple (here, two) branch paths 20, 21 branched in the laminating direction from the radial-direction intermediate position. The other-end sides of the branch paths 20, 21 (radial-direction flow path 17) communicate with the laminating-direction flow paths 18.

The laminating-direction flow paths 18 are formed at regular pitches in the circumferential direction of the rotor 10. Specifically, for cooling the rotor 10, particularly for enhancing the cooling efficiency of the permanent magnets, they are formed between magnet insertion holes 15 (adjacent to the permanent magnets) arranged chevron-wise in their plan views.

Each laminating-direction flow path 18 is formed to penetrate through the rotor 10 in the circumferential direction, while the two sides thereof are opened, thereby providing openings 22, 23 (the refrigerant discharge side openings of the cooling flow path 16) communicating with the outside of the rotor 10.

As described above, the openings 19 of the radial-direction flow paths 17 and the openings 22, 23 of the laminating-direction flow paths 18 are formed at different positions and, when the rotor 10 is in use, supply and discharge of the refrigerant are performed through the openings 19 and 22, 23.

To form the cooling flow path 16, the iron core pieces 11 to 13 differing in shape in their plane views may be laminated.

Specifically, the radial-direction flow path 17 is constituted of part of a penetration hole 24 formed in the iron core piece 12 and a recess 25 formed in the iron core piece 13, while the laminating-direction flow path 18 is constituted of a penetration hole 26 formed in the iron core piece 11, the remaining part of the penetration hole 24 of the iron core piece 12 and a penetration hole 27 formed in the iron core piece 13 (see, for example, Patent Documents 1, 2).

Here, the cooling flow path is not limited to the above structure, but according to the structure of the rotor (for example, the forming position and section shape of the magnet insertion hole), it may also be structured as follows.

The opening of the radial-direction flow path constituting the cooling flow path may not be formed on the shaft hole side of the rotor but may also be formed on the radial-direction outside thereof, or on any one of the laminating-direction (axial-direction) two sides of the rotor. In this case, the radial-direction flow path is not formed in the laminating-direction central portion but can also be formed on one and/or the other sides in the laminating direction.

Also, the radial-direction flow path can also have a structure constituted of a single penetration hole, which means a structure without multiple branch paths.

In the case where the radial-direction flow path includes multiple branch paths, they may be branched toward the shaft hole, whereby multiple openings may be formed on the shaft hole side (see FIG. 3 to be discussed later).

Here, the branch paths may not be branched in the laminating direction but may also be branched on a plane (at the same position in the laminating direction).

Also, the number of branch paths may also be three or more.

Moreover, the radial-direction flow path and laminating-direction flow path may also be inclined relative to the laminating direction.

Further, one cooling flow path may also be constituted of two laminating-direction flow paths divided in the laminating-direction central portion and two radial-direction flow paths respectively communicating with the laminating-direction flow paths (see FIG. 4 to be discussed later).

Next, referring to FIG. 2, description is given of a laminated iron core inspecting apparatus (which may be hereinafter simply called an inspecting apparatus) 30 according to an embodiment of the present invention.

The inspecting apparatus 30 includes a base 31, a columnar shaft part 32 erected on the base 31, and a cylindrical turntable 33 mounted rotatable relative to the shaft part 32. The turntable 33 is used to place the rotor 10 thereon and, using a positioning projection 34 capable of being inserted into the lower portion of the shaft hole 14 of the rotor 10, the rotation center of the turntable 33 and the shaft center of the rotor 10 are made to coincide with each other.

Thus, the rotor 10 can be rotated about the shaft center thereof relative to the base 31.

The inspecting apparatus 30 includes a photosensor 35. The photosensor 35 includes a light projecting part 36 and a light receiving part 37 for detecting the light from the light projecting part 36.

Here, the kind of the photosensor 35 is not limited specifically so long as it includes a light projecting part 36 and a light receiving part 37. For example, a known sensor such as a fiber sensor or a laser sensor can be used.

The photosensor 35 includes the same number of (two) light projecting parts 36 as the two branch paths 20, 21 contained in each cooling flow path 16 (radial-direction flow path 17). Thus, the number of light receiving parts 37 for receiving the light from the light projecting parts 36 is two.

The two light projecting parts 36 are arranged opposite across the shaft center of the rotor 10 and are mounted on a fixed part 38 provided on the upper portion of the shaft part 32 so that they can respectively project lights into the openings 19 of the radial-direction flow paths 17 formed at different positions in the circumferential direction of the rotor 10.

Specifically, the light projecting parts 36 are arranged inclined relative to the vertical direction so that one of the two light projecting parts 36 can project light into the laminating-direction upper branch path 20 and the other can project light into the laminating-direction lower branch path 21, whereby the light projection angles can be adjusted for each of the branch paths 20, 21.

The two light receiving parts 37 are arranged opposite across the shaft center of the rotor 10 and are mounted on the base 31 so that they can detect, through the openings 22, 23, lights from the light projecting parts 36 arranged in the openings 19 of the radial-direction flow paths 17 formed at different positions in the circumferential direction of the rotor 10.

Specifically, the light receiving parts 37 are arranged respectively such that one of them is disposed in the laminating-direction upper (one side in the laminating direction) opening 22 for detecting light from one light projecting part 36, and the other is disposed in the laminating-direction lower (the other side in the laminating direction) opening 23 for detecting light from the other light projecting part 36.

Thus, in the cooling flow paths 16, the penetrating state on the branch path 20 side can be inspected by one pair of the light projecting part 36 and the light receiving part 37, while the penetrating state on the branch path 21 side can be inspected by the other pair of light projecting and receiving parts 36 and 37. Here, in FIG. 2, dotted-line arrows show typically the path of the light from the light projecting part 36 (this applies similarly in FIGS. 3, 4 which are discussed later).

Therefore, when inspecting the penetrating states of the whole cooling flow paths 16, the rotor 10 is rotated using the turntable 33. Here, when, in the inspecting apparatus, a multiple number of photosensors (number of sets of light projecting and receiving parts) are previously prepared, the penetrating states of the whole cooling flow paths 16 can be inspected in a shorter time.

One or both of the light projecting part 36 and the light receiving part 37 can also include a position adjusting mechanism (for example, a cylinder) and/or an angle adjusting mechanism (for example, a cylinder).

In the case where the position adjusting mechanism is equipped in the light projecting part 36, by moving the light projecting part 36 in the axial direction of the rotor 10, for example, variations in the height positions of the openings of the radial-direction flow paths and the height positions of the openings of the radial-direction flow paths formed at different height positions can be coped with; and, by moving the light projecting part 36 in the radial direction of the rotor 10, for example, it can be prevented from come into contact with the key formed in the shaft hole.

Also, in the case where the angle adjusting mechanism (advancing and retreating mechanism relative to the rotor 10) is equipped in the light receiving part 37, the light receiving part 37 can be advanced into the openings, thereby enabling enhancement in the light detection accuracy.

Further, an angle adjusting mechanism can also be equipped in the light projecting part 36 and, in this case, a single light projecting part 36 can cope with multiple branch paths.

A check or determination of the penetrating state of the cooling flow path 16 may preferably be performed using the quantity of light detected by the light receiving part 37.

For example, when the cooling flow path is curved (not straight) and all lights from the light projecting parts are not transmitted to the light receiving parts, the penetrating states may preferably be checked while correcting the received light quantity. Specifically, the received light quantity of the light receiving part is input into a computer (or an operating device), and when a received light quantity equal to or more than a previously set value is obtained, the penetrating state may preferably be determined to be good (that no foreign matters are filled in the cooling flow path 16).

Here, the set value can be set using, for example, a past results value or the like, or can also be set according to the received light quantity (average value) obtained in all cooling flow paths.

Next, referring to FIG. 2, description is given of a laminated iron core inspecting method according to an embodiment of the present invention.

Firstly, the rotor 10 is placed on the turntable 33.

This rotor 10 is in a state after all manufacturing steps such as the arrangement and fixation of a permanent magnet into the magnet-insert hole 15 are finished, that is, in a substantially completed state before a shaft (not shown) is inserted through the shaft hole 14.

The rotor 10 is rotated such that the light projecting parts 36 can be arranged at the forward positions (opposite positions) of the openings 19 of the radial-direction flow paths 17 of the cooling flow paths 16. Here, the inclination of the light projecting parts 36 is previously adjusted for each of the branch paths 20, 21 such that one of the light projecting parts 36 can project a light through the laminating-direction upper branch path 20 and the other can project a light through the laminating-direction lower branch path 21. However, angle adjustment may also be made every measurement.

In this case, it must also be confirmed that the light receiving parts 37 are arranged in the openings 22, 23 of the laminating-direction flow path 18 of the cooling flow path 16.

After end of the above preparation, light projection from the light projecting part 36 is started, and the projected light is received by the light receiving part 37, thereby checking the penetrating state of the cooling flow path 16.

This check is made in all cooling flow paths 16 by rotating the rotor 10 about its axis. Here, this check can be made by performing repeatedly an operation in which, after end of check of one cooling flow path 16, the rotor 10 is rotated by a specific angle and is stopped, and the next cooling flow path 16 is checked. However, by rotating the rotor 10 at low speeds, checks of the respective cooling flow paths 16 can be made successively.

When the penetrating states of the cooling flow paths 16 are good, the rotor 10 is removed from the turntable 33 and is delivered to the next step, and the shaft is inserted into the shaft hole 14.

Here, when the penetrating states of the cooling flow paths 16 are not good, after the rotor 10 is removed from the turntable 33, foreign matters within the cooling flow paths 16 are removed, for example, by air pressure and the above checks are made again.

Thus, even when the penetrating states of the cooling flow paths 16 cannot be visually confirmed, they can be checked highly efficiently and easily. Also, even when the sensor or the like cannot be inserted into the cooling flow paths 16 because they are narrow, the check of the penetrating states is possible.

Here, the light projecting part 36 need not always be mounted on the fixed part 38, but after the rotor 10 is placed on the turntable 33, the part 36 may be inserted into a specific height position from above the shaft hole 14, or a penetration hole may be formed in the axial direction of the turntable and the part 36 may be projected from below the rotor 10.

Figure 3:
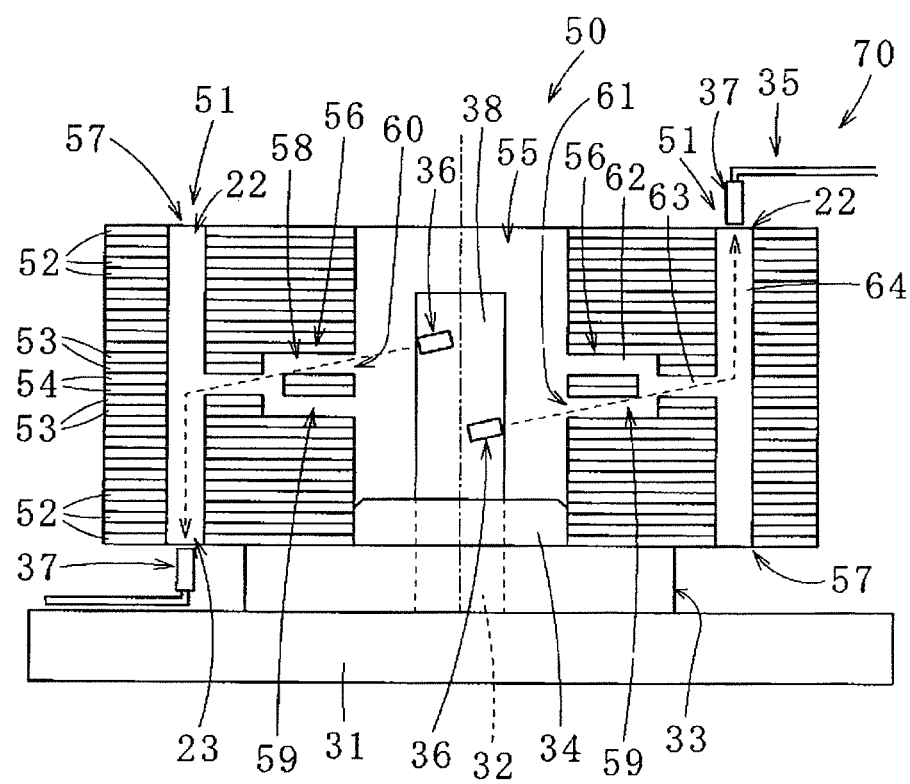
FIG. 3 is an explanatory view of a laminated iron core inspecting method according to another embodiment of the present invention.

Next, referring to FIG. 3, description is given of a rotor (an example of a laminated iron core) 50 to which a laminated iron core inspecting method according to another embodiment of the present invention is applied. The rotor 50 is different from the rotor 10 only in the structure of cooling flow paths 51 constituting the rotor 50. Thus, the same parts are given the same numerals and the specific description thereof is omitted.

The rotor 50 is constituted of multiple laminated annular shaped (predetermined shaped) iron core pieces 52 to 54 and includes a shaft hole 55 formed in the center thereof.

Within the rotor 50, there are formed multiple identically shaped cooling flow paths 51 which are arranged at regular pitches in the circumferential direction of the rotor 50 and through which refrigerant supplied from outside is allowed to flow. Each cooling flow path 51 includes a radial-direction flow path (an example of a first flow path) 56 extending in the radial direction of the rotor 50, and a laminating-direction flow path (an example of a second flow, path) 57 communicating with such radial-direction flow path 56 and extending in the laminating direction of the rotor 50.

The radial-direction flow path 56 is formed in the laminating-direction central portion of the rotor 50 and extends radially with the shaft hole 55 as the center.

The radial-direction flow path 56 includes multiple (here, two) branch paths 58, 59 branched off in the laminating direction from the radial-direction intermediate position. The one-end sides of the branch paths 58, 59 (radial-direction flow path 56) are opened toward the shaft hole 55, thereby providing openings 60, 61 (the refrigerant supply side openings of the cooling flow path 51) communicating with the outside of rotor 50 (the two branch paths 58, 59 join together on the way toward the radial-direction outside).

The laminating-direction flow paths 57 (similarly to the laminating-direction flow paths 18) are formed at regular pitches in the circumferential direction of the rotor 50. Each laminating-direction flow path 57 is formed to penetrate through the rotor 50 in the laminating direction, while the two sides thereof are opened, thereby providing openings 22, 23 (the refrigerant discharge side openings of the cooling flow path 51) communicating with the outside of the rotor 50.

As described above, the openings 60, 61 of the radial-direction flow path 56 are arranged at positions different from those of the openings 22, 23 of the laminating-direction flow path 57. While the rotor 50 is in use, supply and discharge of the refrigerant are carried out through the openings 60, 61, 22, 23.

The cooling flow path 51 is formed by laminating the iron core pieces 52 to 54 differently shaped in their plane views.

Specifically, the radial-direction flow path 56 is constituted of a recess 62 formed in the iron core piece 53 and a portion of a penetration hole 63 formed in the iron core piece 54, while the laminating-direction flow path 57 is constituted of a penetration hole 64 formed in the iron core piece 52 and the other portions of the penetration hole 63 of the iron core piece 54.

Next, referring to FIG. 3, description is given of a laminated iron core inspecting apparatus (which is hereinafter called also an inspecting apparatus simply) 70 according to another embodiment of the present invention. Since the structure of the apparatus 70 is substantially similar to that of the inspecting apparatus 30, the same parts are given the same numerals and thus the specific description thereof is omitted.

The inspecting apparatus 70 includes a photosensor 35 having a light projecting part 36 and a light receiving part 37.

This photosensor 35 includes two light projecting parts 36 correspondingly in number to the two branch paths 58, 59 of one cooling flow path 51. Thus, the number of light receiving parts 37 for receiving lights from the light projecting parts 36 is two.

The two light projecting parts 36, similarly to the rotor 10, are arranged opposite across the shaft center of the rotor 50 and are mounted on a fixed part 38 such that they can project lights through the openings 60, 61 of the different branches 58, 59 of the radial-direction flow paths 56 formed at different positions in the circumferential direction of the rotor 50.

Specifically, the light projecting parts 36 are inclined relative to the vertical direction to thereby adjust the light projection angles for each of the branch paths 58, 59 so that one of the two light projecting parts 36 can project a light into the laminating-direction flow path 57 through the laminating-direction upper branch 58 and the other can project a light into the laminating-direction flow path 57 through the laminating-direction lower branch path 59.

The two light receiving parts 37, similarly to the rotor 10, are also arranged opposite across the shaft center of the rotor 50 and are respectively mounted on and fixed to the base 31 such that they can detect through the openings 22, 23 lights from the light projecting parts 36 respectively arranged in the openings 60, 61 of the different branch paths 58, 59 of the radial-direction flow paths 56 formed at different positions in the circumferential direction of the rotor 50.

Specifically, one of the light receiving parts 37 is arranged in the laminating-direction lower opening 23 such that it can detect the light from one projecting part 36, while the other is arranged in the laminating-direction upper opening 22 such that it can detect the light from the other projecting part 36.

Thus, in the cooling flow paths 51, a check of the penetrating state of the branch path 58 side flow path can be performed by one pair of the light projecting part 36 and the light receiving part 37, whereas a check of the penetrating state of the branch path 59 side flow path can be performed by the other pair of the light projecting part 36 and the light receiving part 37.

Therefore, when checking the penetrating states of all cooling flow paths 51, the rotor 50 is rotated using the turntable 33.

Here, multiple photosensors to be provided in the inspecting apparatus can also be prepared previously. In this case, when the multiple sets of photosensors are arranged at specific angle pitches (for example, 90°, 180°) with the shaft center of the rotor as the center to set the rotor rotation range in a narrow range, the penetrating states of all cooling flow paths can be checked in a shorter time.

Also, when the number of photosensors to be provided in the inspecting apparatus is set for [(number of cooling flow paths)×(number of branch paths)], the penetrating states can be checked at once without rotating the rotor 50. In this case, the turntable 33 can be removed from the inspecting apparatus 70.

Next, referring to FIG. 3, description is given of a laminated iron core inspecting method according to another embodiment of the present invention. Since this inspecting method is substantially similar to the above inspecting method, description is given below briefly.

Firstly, the rotor 50 is placed on the turntable 33.

And, the rotor 50 is rotated such that the light projecting parts 36 can be arranged at the forward positions (opposed positions) of the openings 60, 61 of the radial-direction flow paths 56 of the cooling flow paths 51 and, as the need arises, the inclination of the light projecting parts 36 is adjusted. In this case, it must also be confirmed that the light receiving parts 37 are arranged in the openings 22, 23 of the laminating-direction flow paths 57 of the cooling flow paths 51.

After the above preparation is ended, light projection from the light projecting parts 36 is started and lights projected are received by the light receiving parts 37, thereby checking the penetrating states of the cooling flow paths 51.

This check, similarly to the rotor 10, is made in all cooling flow paths 51 by rotating the rotor 50 once around the shaft center thereof.

Figure 4:
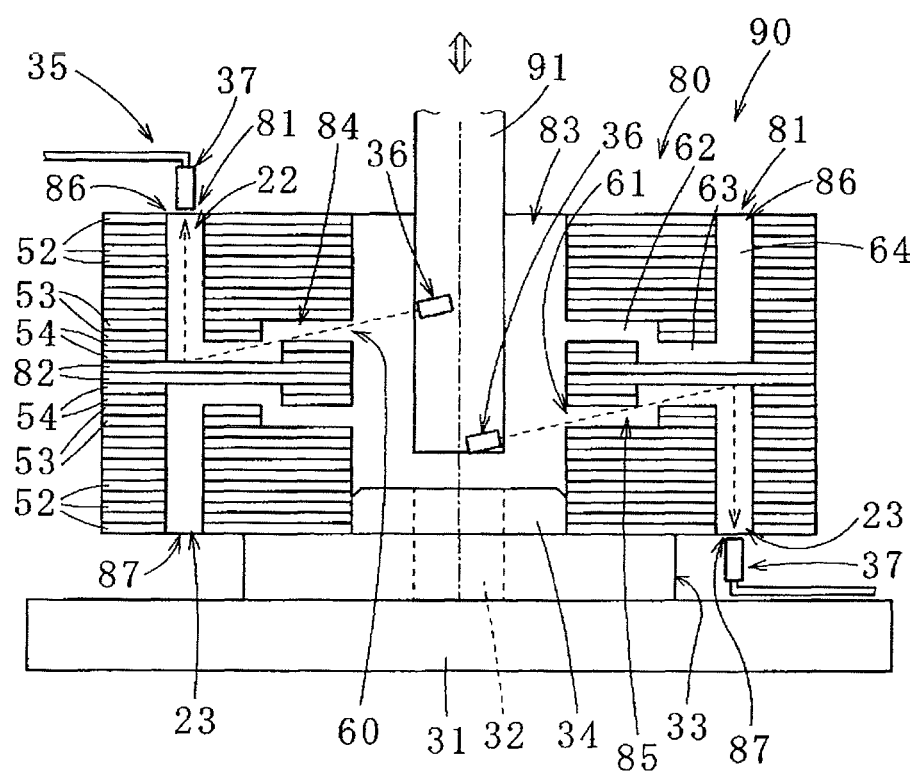
FIG. 4 is an explanatory view of a laminated iron core inspecting method according to a modification.

Further, referring to FIG. 4, description is given of a rotor (an example of a laminated iron core) 80 to which a laminated iron core inspecting method according to a modification. Since the rotor 80 is different from the rotor 50 only in the structure of cooling flow paths 81, the same parts are given the same numerals and thus the specific description thereof is omitted.

The rotor 80 is structured by laminating multiple annular-shaped (predetermined shaped) iron core pieces 52 to 54, 82 and includes a shaft hole 83 formed in the center thereof.

Within the rotor 80, multiple identically shaped cooling flow paths 81, through which a refrigerant supplied from outside is allowed to flow, are formed at regular pitches in the circumferential direction of the rotor 80. The cooling flow paths 81 include radial-direction flow paths (an example of a first flow path) 84, 85 extending in the radial direction of the rotor 80 and laminating-direction flow paths (an example of a second flow path) 86, 87 respectively communicating with the radial-direction flow paths 84, 85 and extending in the laminating direction of the rotor 80.

The radial-direction flow paths 84, 85 are formed in the laminating-direction central portion of the rotor 80 and extend radially with the shaft hole 83 as the center with a clearance between them in the laminating direction.

The one-end sides of the radial-direction flow paths 84, 85 are opened toward the shaft hole 83, thereby providing openings 60, 61 communicating with the outside of the rotor 80.

The laminating-direction flow paths 86, 87 are formed at regular pitches in the circumferential direction of the rotor 80 while they are divided in the laminating-direction central portion.

The lower end of the laminating-direction upper flow path 86 communicates with the other end of the radial-direction flow path 84 and the upper end thereof is opened, thereby providing the opening 22 communicating with the outside of the rotor 80. Also, the upper end of the laminating-direction lower flow path 87 communicates with the other end of the radial-direction flow path 85 and the lower end thereof is opened, thereby providing the opening 23 communicating with the outside of the rotor 80.

The cooling flow path 81 is formed by laminating iron core pieces 52 to 54, 82 differently shaped in their plane views.

Specifically, the radial-direction flow paths 84, 85 are constituted of a recess 62 formed in the iron core piece 53 and a portion of a penetration hole 63 formed in the iron core piece 54, while the laminating-direction flow paths 86, 87 are constituted of a penetration hole 64 formed in the iron core piece 52 and the remaining portion of the penetration hole 63 of the iron core piece 54.

Next, referring to FIG. 4, description is given of a laminated iron core inspecting apparatus (which is hereinafter called also an inspecting apparatus simply) 90 and an inspecting method according to the modification. Since they are substantially similar in structure to the inspecting apparatus 70 and inspecting method, the same parts are given the same numerals and thus the specific description thereof is omitted.

The inspecting apparatus 90 includes a photosensor 35 having a light projecting part 36 and a light receiving part 37. The photosensor 35 includes two light projecting parts 36 formed identically in number with the radial-direction flow paths 84, 85 and laminating-direction flow paths 86, 87 included in one cooling flow path 81. Thus, the number of light receiving parts 37 for receiving lights from the light projecting parts 36 is two.

The two light projecting parts 36, similarly to the case of the rotor 50, are arranged opposite across the shaft center of the rotor 80 and are mounted on a lifting rod 91 such that they respectively can project lights into the openings 60, 61 of the radial-direction flow paths 84, 85 formed at different positions in the circumferential direction of the rotor 80. Thus, the inspecting apparatus 90 excludes the fixed part 38.

Specifically, one of the light projecting parts 36 can project a light into the laminating-direction flow path 86 through the laminating-direction upper radial-direction flow path 84, while the other can project a light into the laminating-direction flow path 87 through the laminating-direction lower radial-direction flow path 85.

The two light receiving parts 37, similarly to the case of the rotor 50, are also arranged opposite across the shaft center of the rotor 80 and are fixedly mounted on the base 31 such that they can detect, through the openings 22, 23, lights from the light projecting parts 36 disposed in the different openings 60, 61 of the radial-direction flow paths 84, 85 formed at different positions in the circumferential direction of the rotor 80.

Specifically, one of the light receiving parts 37 is arranged in the laminating-direction upper opening 22 for detecting the light from one light projecting part 36, while the other is arranged in the laminating-direction lower opening 23 for detecting the light from the other light projecting part 36.

Thus, in the cooling flow paths 81, a check for the penetrating state of the radial-direction flow path 84 side flow paths can be made by one pair of the light projecting part 36 and the light receiving part 37, while a check or the penetrating state of the radial-direction flow path 85 side flow paths can be made by the other pair of the light projecting part 36 and the light receiving part 37.

Therefore, when checking the penetrating states of all cooling flow paths 81, the rotor 80 is rotated using the turntable 33.

Here, the light projecting parts 36, after the rotor 80 is placed onto the turntable 33, may be arranged by inserting the lifting rod 91 to a specific height position from above the shaft hole 83.

Although the present invention has been described heretofore with reference to the embodiments thereof, the present invention is not limited to the embodiments at all but contains other embodiments and modifications that are possible within the scope of the appended patent claims. For example, the above-mentioned embodiments and modification can be partially or wholly combined together to structure methods and apparatus for inspecting a laminated iron core according to the present invention. Such methods and apparatus fall under the scope of the rights of the present invention.

Also, in the above embodiments, description has been given of an example in which the laminated iron core inspecting methods and apparatus of the present invention are applied to a rotor that is a rotor laminated iron core. However, for example, in order to reduce the influence of heat from the rotor, the present invention can also be applied to a stator (stator core) that is a stator laminated iron core.

And, in the above embodiments, description has been given of a case where, by rotating the rotor relative to the fixed photosensor, the penetrating states of the respective cooling flow paths are inspected sequentially. However, the photosensor can also be rotated relative to the fixed rotor.

What is claimed is:

1. A method for inspecting a laminated iron core, the method comprising:
    providing the laminated iron core including a plurality of iron core pieces laminated together and a cooling flow path:
    wherein the cooling flow path allows refrigerant to flow therethrough and to be supplied and discharged through openings of the cooling flow path that are formed at different positions,
    arranging a light projecting part and a light receiving part of a photosensor in the openings of the cooling flow path, respectively, such that at least one of the light projecting part and light receiving part is positioned at an inner periphery of the plurality of iron core pieces that are laminated together; and
    detecting light from the light projecting part by the light receiving part to thereby inspect a penetrating state of the cooling flow path.

2. The method according to claim 1, wherein the cooling flow path includes a first flow path extending perpendicularly to a laminating direction of the laminated iron core and a second flow path communicating with the first flow path and extending in the laminating direction of the laminated iron core, and
    the light projecting part is arranged in the opening of the first flow path, and the light receiving part is arranged in the opening of the second flow path.

3. The method according to claim 2, wherein the laminated iron core includes at least one other cooling flow path to form a plurality of cooling flow paths in a circumferential direction of the laminated iron core, and
    the laminated iron core and the photosensor are relatively rotated about a shaft center of the laminated iron core and the penetrating states of the plurality of cooling flow paths are sequentially inspected.

4. The method according to claim 3, wherein each first flow path is branched off to have a plurality of branch paths communicating with the second flow path, and
    at least a same number of the light projecting parts as a number of the plurality of branch paths included in each first flow path are arranged in the openings of the first flow path formed at different positions in the circumferential direction of the laminated iron core, and projection angles of lights from the light projecting parts are adjusted for each of the branch paths.

5. The method according to claim 3, wherein each first flow path is branched off to have a plurality of branch paths respectively including the openings of the first flow path, and at least a same number of the light projecting parts as a number of the plurality of branch paths included in each first flow path are arranged in the openings of the different branch paths of the first flow paths formed at different positions in the circumferential direction of the laminated iron core, and projection angles of lights from the light projecting parts are adjusted for each of the branch paths.

6. The method according to claim 1, wherein determination of the penetrating state of the cooling flow path is made using a quantity of light detected by the light receiving part.

7. An apparatus for inspecting a laminated iron core structured by laminating a plurality of iron core pieces having a predetermined shape and including therein a cooling flow path allowing refrigerant to flow therethrough, the refrigerant being supplied and discharged through openings formed at different positions, the apparatus comprising:

a photosensor including a light projecting part and a light receiving part arranged in the openings of the cooling flow path, respectively, wherein at least one of the light projecting part and light receiving part is positionable at an inner periphery of the plurality of iron core pieces laminated together, and the apparatus detects light from the light projecting part by the light receiving part to thereby inspect a penetrating state of the cooling flow path.

8. The apparatus according to claim 7, wherein the cooling flow path includes a first flow path extending perpendicularly to a laminating direction of the laminated iron core and a second flow path communicating with the first flow path and extending in the laminating direction of the laminated iron core, and the light projecting part is arranged in the opening of the first flow path, and the light receiving part is arranged in the opening of the second flow path.

9. The apparatus according to claim 8, wherein the first flow path includes a plurality of branch paths, at least a same number of light projecting parts as a number of branch paths are arranged, and projection angles of lights from the light projection parts are adjusted for each of the branch paths.

10. The apparatus according to claim 7, further comprising a turntable which rotates the laminated iron core about a shaft center of the laminated iron core.

11. The apparatus according to claim 7, wherein one or both of the light projecting part and the light receiving part include a position adjusting mechanism.

12. The apparatus according to claim 7, wherein one or both of the light projecting part and the light receiving part include an angle adjusting mechanism.

* * * * *